May 13, 1975 O. L. WEEKS Plant Pat. 3,719
ROSE PLANT
Filed March 21, 1974
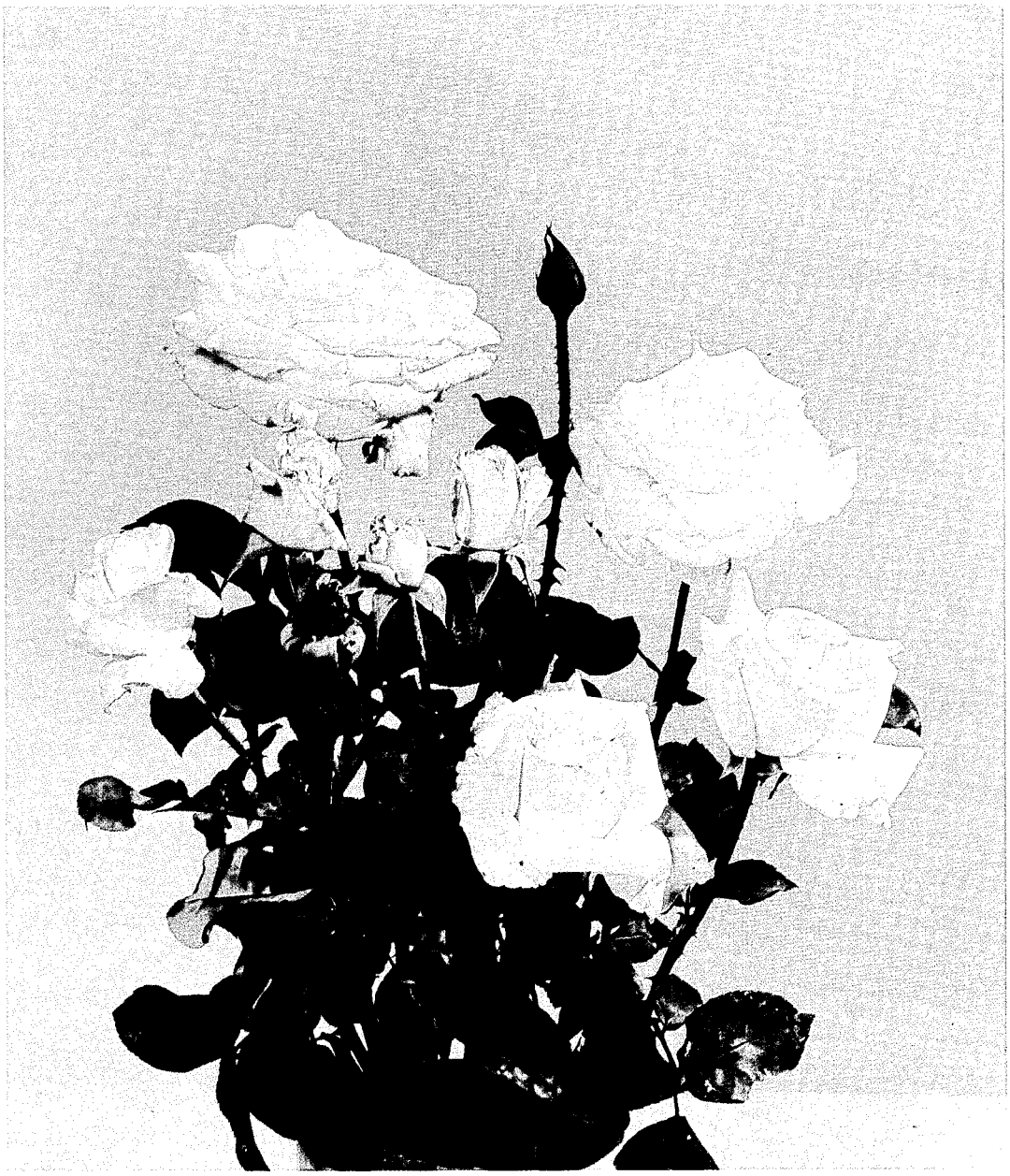

United States Patent

Plant Pat. 3,719

Patented May 13, 1975

3,719

ROSE PLANT

O. L. Weeks, 926 W. Philadelphia,
Ontario, Calif. 91762

Filed Mar. 21, 1974, Ser. No. 453,385

Int. Cl. A01h *5/00*

U.S. Cl. Plt.—14 1 Claim

The present invention relates to a new and distinct variety of rose plant of the hybrid tea class, which was originated by me by crossing two unnamed and unpatented rose seedlings, respectively identified in my breeding records as #604–A–16 and #6122–C–97, the former being the seed parent and the latter the pollen parent.

As the result of this breeding, I have produced a new and improved rose variety which is distinguished from its parents, as well as from all other rose varieties of which I am aware, as evidenced by the following unique combination of characteristics which are outstanding in the new variety:

(1) An extremely vigorous habit of growth, with production of exceptionally long and strong stems which are capable of supporting the heavy blooms well;
(2) An extraordinarily profuse blooming habit and excellent and amazingly rapid repetition of the blooming cycle when the plant is pruned back;
(3) The production of unusually long buds which open to large beautifully formed open flowers of a classic exhibition type and having many petals;
(4) A gardenia-like quality and unusually good substance of the flower petals which is uncommon in most white-flowered varieties; and
(5) A creamy-white flower color less than pure stark white, but still definitely giving the flowers an overall white-effect when the plants are in heavy bloom.

In comparison with its pollen parent, the plant of my new variety is much more vigorous and free-blooming; its flowers are much larger, more fully petalled and more elegantly shaped than those of this parent; and the flower color is a creamy white in contrast to the pale yellow flower color of the parent variety.

As compared with its seed parent, the plant of my new variety has considerably greater vigor and overall growth habit; it is a notably more profuse bloomer; and the flowers of the new variety are much larger and have much better petal substance, while being of a similar color.

Asexual reproduction of my new rose variety by budding, as perofrmed by me at Ontario, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Munsell's Color Cascade, published by Munsell Color Company, Inc., of Baltimore, Md., except where general color terms of ordinary dictionary significance are obvious:

Type: Hardy; tall; outdoor; seedling; for cut flowers and for garden decoration.
Class: Hybrid tea.
Breeding: Seedling.
*Seed parent.*—An unnamed seedling.
*Pollen parent.*—An unnamed seedling.

Propagation: Holds its distinguishing characteristics through succeeding propagations by budding.

FLOWERS

Locality where grown and observed: Ontario, Calif.
Flowers borne: Singly; on strong stems of from medium to long length.
Quantity of bloom: Free and abundant, both outdoors and in greenhouse.
Continuity: One season; from intermittent to continuous.
Fragrance: Slight. Nature—Tea.
Bud:
*Peduncle.*—Medium length; medium heavy caliper; erect; stiff; entirely smooth. Color—From light to medium green.
*Before calyx breaks.*—Size—Small. Form—From short to medium length; pointed; with a conspicuous neck; with foliaceous appendages on the surface of the bud; with slender bristle-like foliaceous parts extending beyond the tip of the bud less than ¼ of its length.
*As calyx breaks.*—Color—Pale Yellow, between 25–4 and 26–4, blending to 25–3.
*As petals first open.*—Size—Small. Form—Short. Color—Outside—Basal half Strong Yellow, blending upward to Pale Yellow, between 25–1 and 26–1. Inside—Basal segment of Strong Yellow, 25–6, gradually fading half-way to apex, then progressing into Pale Yellow, between 26–2 and 26–1.
*Opening.*—Opens up well.
Bloom:
*Size (when fully open).*—From medium to large; from 3 inches to 4 inches.
*Petalage.*—Double; from 28 to32 petals.
*Form.*—High-centered at first, but becoming fairly flat and open cupped; petals being at first tightly cupped and rolled outward, but later becoming loosely cupped and rolled outward at maturity.
Petals:
*Texture.*—Moderately thick and soft.
*Appearance.*—Inside—From satiny to velvety. Outside—From satiny to velvety.
*Shape.*—Outside—Mostly round, with apex flat. Intermediate—Round. Inside—Mostly round, with apex flat.

This description of a newly opened flower was made from a rose grown outdoors in the month of October, at Ontario, Calif.:

*Color.*—Outer petal—Outside surface—Basal color of Strong Yellow, between 25–5 and 25–4 extending half-way up petal in center, blending into Pale Yellow, between 25–1 and 26–1. Inside surface—Basal segment of Strong Yellow, 25–5 extending half-way up petal in center, blending into Pale Yellow, between 25–1 and 26–1. Intermediate petal—Outside surface—Basal color of Strong Yellow, between 26–5 and 26–4 extending half-way up petal in center, blending to Pale Yellow, between 26–1 and 26–2. Inside surface — Basal color of Strong Yellow, between 26–5 and 26–6 extending half-way up center of petal, blending to Pale Yellow, between 26–1 and 26–2. Inner petal—Outside surface—Basal color of Strong Yellow, 26–5 extending half-way up center of petal to Pale Yellow, between 26–3 and 26–2, with a very faint light pink tinge. Inside surface—Basal color of Strong Yellow, 26–6, blending into Pale Yellow, between 26–4 and 26–3.

This description was made from a rose that was open for three days outdoors in the month of October at Ontario, Calif.:

*Color.*—Outer petal—Outside surface—Basal segment of Pale Yellow, between 25–3 and 25–4, blending upward to Paler Yellow, between 26–2 and 26–1. Inside surface—Basal segment of Pale to Strong Yellow, 24–3, blending into Pale Yellow 26–1 and 26–2. Inner petal—Outside surface—Basal segment of Strong Yellow, between 25–5 and 25–4, blending into Pale Yellow, between 25–1 and 26–1. Inside surface—Basal segment of Strong Yellow, between 26–5 and 26–6, blending into Pale Yellow, between 25–1 and 26–1.

*General color effect.*—Newly opened flower—Combination between Pale Yellow, 26–2 and 26–1, but with an occasional showing of Strong Pink, 38–4. 3-days open—Between Pale Yellow, 26–2 and 26–1, blending to even fainter Yellow, between 26–1 and 26–2.

*Behavior.*—Drops off cleanly.

*Flower longevity.*—On bush in garden—2 or 3 days in October. Cut roses grown outdoors and kept at living room temperatures—2 or 3 days in October.

REPRODUCTIVE ORGANS

Stamens: Many; arranged irregularly about pistils; tucked in calyx.

Filaments: Medium length; most with anthers. Color—Yellowish white.

Anthers: Medium large; open at various times. Color—Striped light and dark brown.

Pollen: Abundant. Color—From white to lemon.

Pistils: From medium number to many.

Styles: Uneven; mostly short lengths; thin caliper; bunched.

Stigma: Color—Yellow.

Ovaries: All enclosed in calyx.

Hips: None observed.

Sepals: Permanent; moderately short; spear-shaped; recurved. Color—Medium green with a little reddish overtone in the early stages.

Seeds: None observed.

PLANT

Foliage:

*Leaves.*—Compound of 3, 5 and 7 leaflets; normal abundance; medium size; moderately leathery.

*Leaflets.*—Shape—Primarily ovate, but with a little more elongated point. Apex—Obtuse. Base—Fairly round. Margin—Serrate.

*Color.*—Mature—Upper surface—Moderately dark green. Under surface—Moderately light green. Young—Upper surface—Moderately dark bronze to red. Under surface—Moderately light red. Rachis (the supporting stem of the compound leaf) — From medium to heavy caliper. Upper side—Smooth. Under side—Somewhat prickly.

*Stipules.*—Medium long; medium wide; from medium to long points turning out at an angle of less than 45°.

Disease resistance: Above average resistance to powdery mildew even though flower color is a pale yellowish white, as determined by comparison with other rose varieties grown under the same conditions at Ontario, Calif.

Growth:

*Habit.*—Bushy; upright; much branched.

*Growth.*—Very free and vigorous.

*Canes.*—Heavy caliper.

*Main stems.*—Color—Green. Large prickles—Several; medium long; straight, but some hooked downward; with medium long, oval base. Color—Light brown. Small prickles—None to few. Color—Brown. Hairs—None.

*Branches.*—Color—Dull grey-green. Large prickles—Few to several; medium long; hooked downward; with long, narrow, somewhat oval base. Color—Light brown. Small prickles—Several. Color—From brown to reddish. Hairs—None.

*New shoots.*—Color—Dull red. Large prickles—Several; medium long; hooked downward; with long, narrow, rounded base. Color—Reddish brown, with light green tip. Small prickles—From few to several. Color—Reddish brown. Hairs—Few.

I claim:

1. A new and distinct variety of rose plant of the hybrid tea class, substantially as herein shown and described, characterized particularly as to novelty by the unique combination of an extremely vigorous habit of growth, with production of exceptionally long and strong stems which are capable of supporting the heavy blooms well, an extraordinarily profuse blooming habit and excellent and amazingly rapid repetition of the blooming cycle when the plant is pruned back, the production of unusually long buds which open to large beautifully formed open flowers of a classic exhibition type and having many petals, a gardenia-like quality and unusually good substance of the flower petals which is uncommon in most white-flowered varieties, and a creamy-white flower color less than pure stark white, but, still definitely giving the flowers an overall white effect when the plants are in heavy bloom.

No references cited.

ROBERT E. BAGWILL, Primary Examiner